(12) United States Patent
Delisle

(10) Patent No.: US 7,963,904 B2
(45) Date of Patent: *Jun. 21, 2011

(54) METHOD AND DEVICE FOR TREATING BODY AILMENTS

(76) Inventor: Clarence A. Delisle, Windsor (CA)

( * ) Notice: Subject to any disclaimer, the term of this patent is extended or adjusted under 35 U.S.C. 154(b) by 1714 days.

This patent is subject to a terminal disclaimer.

(21) Appl. No.: 10/906,885

(22) Filed: Mar. 10, 2005

(65) Prior Publication Data

US 2005/0159638 A1    Jul. 21, 2005

Related U.S. Application Data

(63) Continuation-in-part of application No. 10/398,079, filed as application No. PCT/IB01/02335 on Sep. 28, 2001, now Pat. No. 7,264,585.

(60) Provisional application No. 60/236,340, filed on Sep. 29, 2000.

(51) Int. Cl.
*A61N 1/00* (2006.01)

(52) U.S. Cl. ......................................................... 600/14

(58) Field of Classification Search ................ 600/9–15; 128/897, 898
See application file for complete search history.

(56) References Cited

U.S. PATENT DOCUMENTS

| | | | | |
|---|---|---|---|---|
| 96,044 A | * | 10/1869 | Smith | ............................. 600/13 |
| 1,535,618 A | | 4/1925 | Mayer | |
| 1,922,696 A | * | 8/1933 | Hardage | ....................... 200/431 |
| 4,266,533 A | | 5/1981 | Ryaby et al. | |
| 5,131,904 A | | 7/1992 | Markoll | |
| 5,669,868 A | | 9/1997 | Markoll | |
| 5,908,844 A | | 6/1999 | Azure | |
| 6,149,577 A | * | 11/2000 | Bouldin et al. | ................. 600/13 |
| 7,264,585 B2 | * | 9/2007 | Delisle | ............................ 600/14 |
| 2005/0101827 A1 | | 5/2005 | Delisle | |

FOREIGN PATENT DOCUMENTS

| | | |
|---|---|---|
| WO | WO9104102 | 4/1991 |
| WO | WO0226322 | 4/2002 |

OTHER PUBLICATIONS

International Search Report for PCT/IB2001/002335, Mar. 21, 2002, 4 pages.

* cited by examiner

*Primary Examiner* — Samuel G Gilbert

(74) *Attorney, Agent, or Firm* — Reising Ethington P.C.

(57) ABSTRACT

An apparatus and a method for treating ailments of the human body by electromagnetic waves. The body part to be treated is located inside an induction coil and the coil is energized by a switching device that supplies the coil with current pulses that include higher frequency components that occur during at least a portion of the pulse. Both manual and electronic switching devices are disclosed. The manual switching device uses manually operable striking contactors and the high frequency components are generated by arcing between the contactors. The automatic switching device is an electronic controller that simulates the current pulses produced using the manual method.

12 Claims, 3 Drawing Sheets

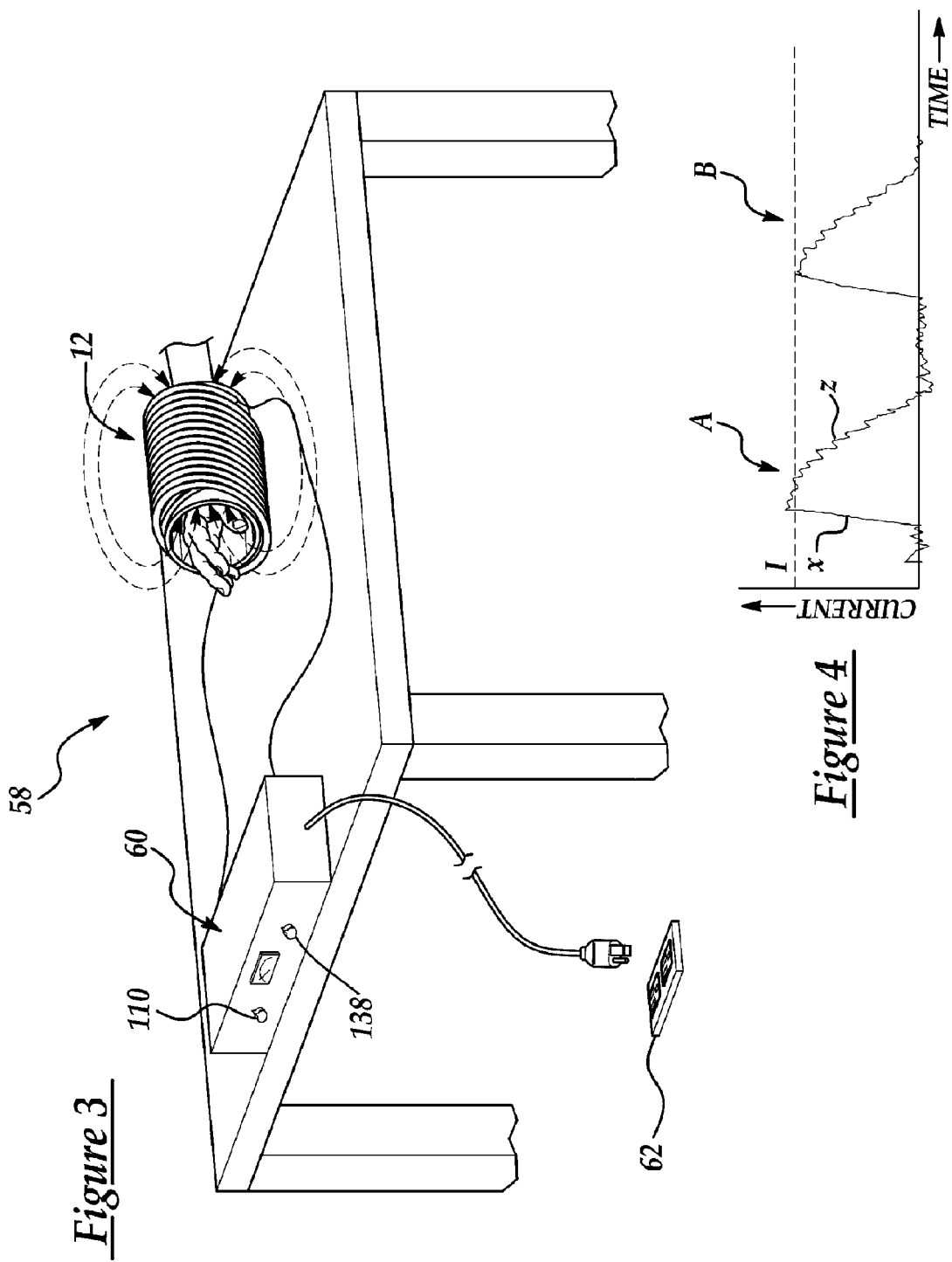

METHOD AND DEVICE FOR TREATING BODY AILMENTS

CROSS-REFERENCE TO RELATED APPLICATION

This application is a continuation-in-part of U.S. application Ser. No. 10/398,079 which is a 35 U.S.C. §371 National Stage of PCT/IB01/02335 filed Sep. 28, 2001, which in turn claims the priority of Provisional Application No. 60/236,340, filed Sep. 29, 2000. Both of these prior applications are incorporated herein by reference.

TECHNICAL FIELD

This invention relates to a method and device for treating ailments of the human body; more particularly, it relates to an improved method and device for using an electromagnetic field as a therapeutic agent for providing pain relief of certain ailments such as arthritis.

BACKGROUND OF THE INVENTION

Therapeutic devices and methods using a magnetic field for treating various diseases, including arthritis, are already known in the prior art.

There are numerous teachings in the prior art for the application of a magnetic field to living tissue for healing and/or relief of pain. For example, U.S. Pat. No. 3,658,051, granted Apr. 25, 1972, discloses a process and apparatus for the treatment of human tissue where a body part to be treated is placed between the poles of an electromagnet. A pulsed magnetic field is applied to the body part which is induced in the electromagnet by an intermittent direct current. As further examples, U.S. Pat. No. 4,177,796, granted Dec. 11, 1979, U.S. Pat. No. 4,758,429, granted Jul. 19, 1988, and U.S. Pat. No. 5,314,400, granted May 24, 1994, disclose devices and methods for treating human joints, tissue, and various areas of the body using the application of a magnetic field.

Various processes and devices are known in the prior art for use in treating ailments and diseases in humans and in animals which utilize a magnetic field that may be induced by currents flowing through solenoids or coils. For example, the group of related patents comprises U.S. Pat. No. 5,131,904 granted Jul. 21, 1992, U.S. Pat. No. 5,453,073 granted Sep. 26, 1995 and U.S. Pat. No. 5,842,966 granted Dec. 1, 1998, and discloses a process for the treatment of arthritis through the application of an electromagnetic field to a body part, where the device consists of a circular tube containing a coil, and where the coil segments are separated by air gaps. A pulsed DC voltage is applied to the coil which generates an electromagnetic field.

As a further example, U.S. Pat. No. 4,757,804 granted Jul. 19, 1988, discloses a method and apparatus for treating human tissue through the application of a pulsed magnetic field, where a flexible belt capable of carrying a pulsed electrical signal encircles the body part to be treated. The belt has a plurality of parallel conductors extending along its length to form at least one continuous coil.

SUMMARY OF THE INVENTION

In accordance with this invention, an electromagnetic treatment device is provided which can be used for treating ailments of the human body or the body of other living creatures by applying an electromagnetic field to selected parts of the body. The treatment device includes an induction coil and a switching device for supplying current pulses to the induction coil so that it generates an electromagnetic field in a selected part of the body. The switching device has an input for receiving operating power from a battery or other source of power, and has an output connected to the induction coil. The current pulses supplied to the induction coil include higher frequency components that occur during either the entire pulse or just during the trailing edge or other portion of the pulse. The average amount of current delivered to the coil can be controlled using the switching device by, for example, controlling the repetition rate or pulse length of the pulses.

BRIEF DESCRIPTION OF THE DRAWINGS

Preferred exemplary embodiments of the invention will hereinafter be described in conjunction with the appended drawings, wherein like designations denote like elements, and wherein:

FIG. 3 depicts another embodiment of an electromagnetic wave treatment device in accordance with a second aspect of this invention, where an electronic power supply is used;

FIG. 4 shows a waveform diagram representing the current pulses supplied by the electronic controller of FIG. 3.

DETAILED DESCRIPTION OF THE PREFERRED EMBODIMENTS

Figure 1:
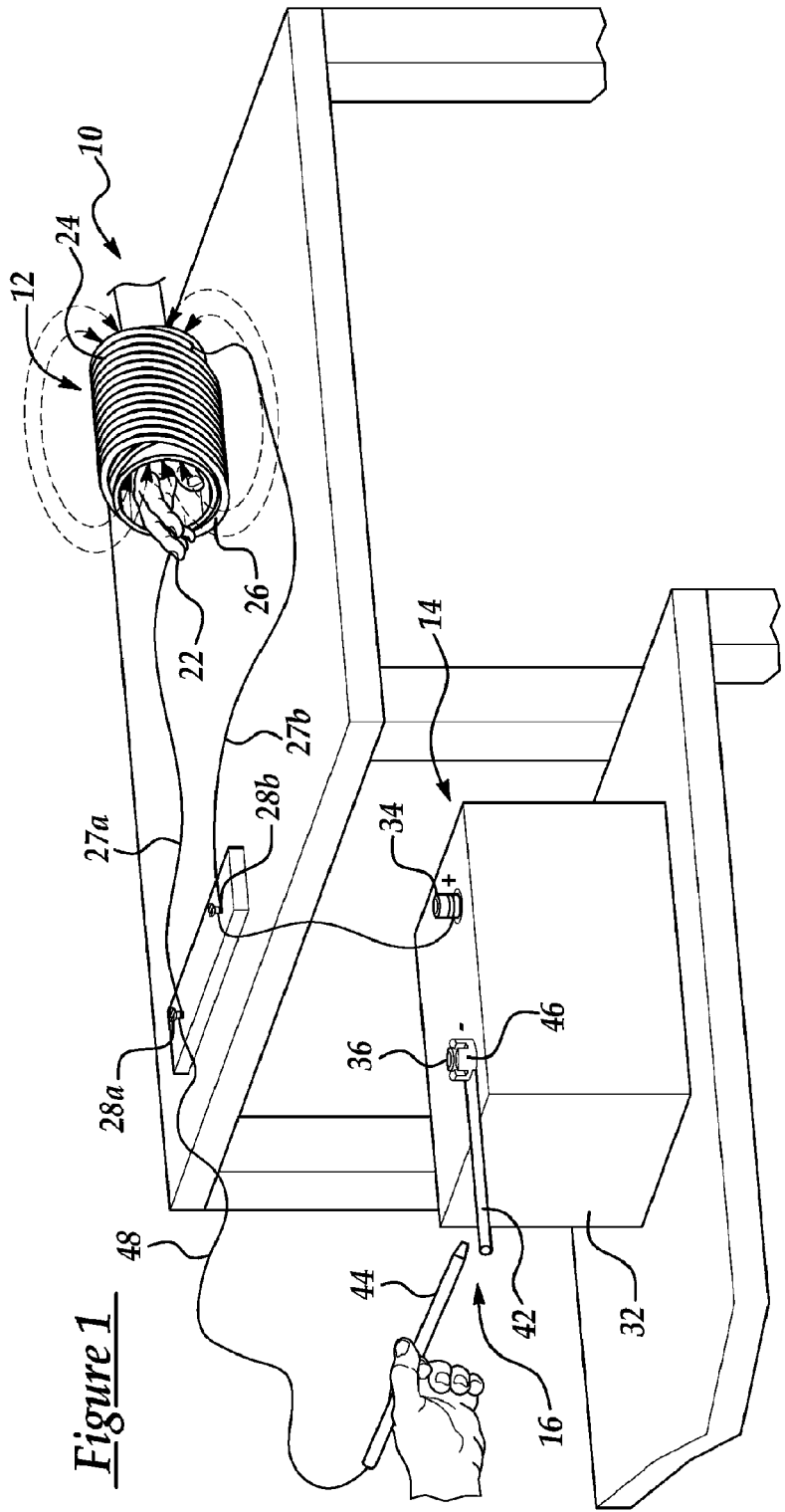
FIG. 1 depicts an embodiment of an electromagnetic wave treatment device in accordance with a first aspect of this invention, where a manually-operated switching device is used.

Referring now to the drawings, several illustrative embodiments of the device and method of this invention will be described with reference to the treatment of arthritis. It will be appreciated as the description proceeds, that the invention is useful in many other applications and for treating many other ailments, and may be realized in a wide variety of embodiments.

As shown in FIG. 1, an electromagnetic treatment device 10 comprises, in general, an induction coil 12 adapted to generate an electromagnetic field for application to a selected part of a person's body. In this first embodiment, the induction coil 12 is energized by a DC power source 14 through a manually-operated switching device 16 connected in a series circuit arrangement.

Induction coil 12 is a generally cylindrical-shaped component that generates an electromagnetic field and generally comprises a coil-form 22 for supporting a coil winding 24. The coil-form 22 is preferably a hollow, tubular-shaped component constructed of insulated, non-magnetic material such as cardboard or plastic, which is sufficiently rigid to support coil winding 24 and to sustain its configuration. The hollow coil-form defines a space having a cross-sectional shape that is adapted to receive the selected part of the body which is to be treated, such as the wrist, ankle, lower torso, etc. Coil winding 24 is wound around coil form 22 with a single strand of magnet wire 26 which terminates in first and second leads 27a and 27b. The coil winding has multiple adjacent turns forming a helix that extends generally in the axial direction. The number of turns is determined by the particular application for which the magnetic treatment device 10 is used. A terminal block adjacent coil-form 22 includes a pair of binding posts 28a and 28b for facilitating connection of coil winding 24 to power source 14 through switching device 16. For this purpose, lead 27a is connected to binding post 28a, and lead 27b is connected to binding post 28b.

The DC power source 14 in this illustrative embodiment suitably comprises a battery 32 having a positive terminal 34 and a negative terminal 36. Battery 32 can be a conventional 12 volt, acid storage battery of the type currently used on automobiles for supplying current to the starter motor and other accessories. However, other types of power sources, such as 110 VAC source can be used as well.

Switching device 16 provides intermittent electrical current to induction coil 12, and includes a fixed striking contactor 42 and a manually movable striking contactor 44. The fixed contactor 42 is a conductive metal rod electrically and physically connected to the negative terminal 36 of battery 32 by a suitable battery clamp 46. The movable striking contactor 44 is also a conductive metal rod, which is electrically connected at one end of a flexible insulated copper wire 48. The other end of wire 48 is connected to lead 27a via binding post 28a. The movable striking contactor 44 is adapted to be hand-held by an operator of the treatment device 10 for intermittent striking against the fixed striking contactor 42. Switching device 16 may also take the form of a conventional single pole, double throw switch or an electronic circuit, as well as a number of other switching devices known in the art.

The method of the first embodiment will now be described with reference to the magnetic treatment device 10 shown in FIG. 1. In preparation for treatment, the portion of the person's body to be treated, such as the hand, is inserted into the hollow space of induction coil 12, which is preferably open at both axial ends. In this location, the hand is subjected to the maximum electromagnetic field generated by induction coil 12. The treatment process includes applying a sequence of electrical pulses to coil form 22, which in turn generates a series of corresponding electromagnetic field pulses. Each electromagnetic pulse is generated under control of the person operating the treatment apparatus. Each pulse is produced by manual striking of the movable striking contactor 44 against the fixed contactor 42. The striking engagement of the contactors may be executed by the operator with variations of engagement force, duration and quickness of separation of the contactors. The pulse repetition rate may also be varied by the operator such that the time between adjacent pulses may be substantially uniform or widely non-uniform. These variables in operation of the switching contactors enable the operator to exercise regulation of the strength of the electromagnetic field during a pulse, the duration of a pulse and the time between successive pulses in the pulse train generated during a treatment session. The operator may adjust one or more of the variables so as to subject the selected body part to more or less electromagnetic field strength in a time variable pattern in order to optimize the benefit of the treatment session. Also, the operator may need to exercise discretion in regard to possible overheating of the induction coil and the striking contactors by the current supplied to the coil. For example, applying large contact pressure to the contactors for an extended time period may result in elevated temperatures which are uncomfortable to the person being treated or the operator. On the other hand, the current may be increased if desired by reducing the contact resistance of the contactors by wetting them with tap water or, in some cases, by removing metal oxides. Examples of electromagnetic pulse patterns of treatment will be given below.

Figure 2:
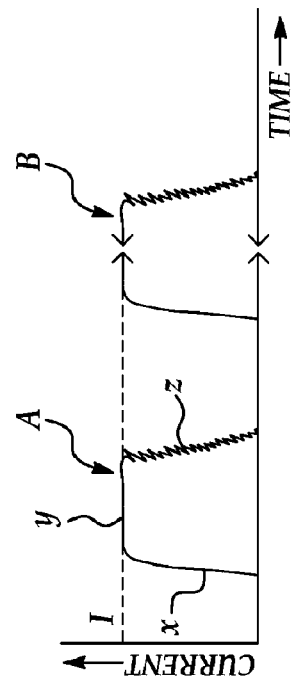
FIG. 2 shows a waveform diagram which represents the current in an induction coil which generates an electromagnetic wave in accordance with the device of FIG. 1.

With reference to FIG. 2, there is shown a representation of waveforms A and B of two successive pulses which are produced by operation of the switching device 16 of the first embodiment. When the movable contactor 44 strikes the fixed contactor 42 the switching device 16 is in a closed state which initiates current through the contactors which rapidly increases in magnitude as represented by the leading edge x of the waveform A. The current waveform reaches a maximum value I and has a substantially flat top y and constant value until the movable contactor is separated from the fixed contactor which places the switching device in open state. Upon initial separation of the contactors the trailing edge z of the waveform commences and in a brief time interval, declines to zero. During the trailing edge, an arc discharge occurs in the air gap between the contactors due to the inductive impedance of the induction coil 12 which tends to maintain the current through the coil until the energy stored in the electromagnetic field of the coil has dissipated. The magnitude of the current I through the coil is sufficiently high so that the collapsing field of the coil generates a high voltage energy at a voltage spike as a back electromotive force high enough to ionize the air gap atmospheric gases which conduct the current until the energy in the field of the coil is dissipated. Thus, an arc discharge or plasma is generated in the atmospheric gases between the contactor while the magnitude of the current diminishes from the maximum value I to zero. This produces an arc discharge which is visible to the human eye in daylight. The current pulse B has the same waveform as pulse A except that it may be of longer or shorter duration as indicated by the arrow head interruption along the time axis of the waveform of pulse B.

The current pulses, as represented by pulses A and B, through the induction coil 12 generate electromagnetic field pulses corresponding to the current fluctuations. The electromagnetic field produced by each pulse has its greatest magnetic field strength concentrated in the interior space of the coil-form while a weaker magnetic field is produced in the space surrounding the outside of the coil-form. The leading edge x of the current pulse produces an electromagnetic field which includes a wide spectrum of electromagnetic wave frequency components. During the interval of the flat top y of the waveform, the current may be substantially constant or may undergo relatively small variations due to changing contact resistance between the contactors (arising, for example, from relative movement of the contactors). Consequently, during the flat top y portion of the waveform the electromagnetic field is predominately a static magnetic field to the extent that the current flow remains constant. During the interval of the trailing edge z, a complex current waveform is generated which is initiated by the high energy voltage spike as discussed above. This complex current waveform produces a corresponding complex electromagnetic waveform. At the termination of the trailing edge of the waveform, the coil returns to a quiescent state.

The generation of the electromagnetic field by the treatment apparatus 10 will now be discussed more specifically. An important parameter in the design of the induction coil 12 in conjunction with the selected power source 14 is the ampere turns AT to be used for generating the electromagnetic field of the coil. The value of AT is the product of the number of turns in the coil and the number of amperes delivered to the coil by the power source. The magnetic flux density B, in Teslas (T) generated at a point, including the center of the coil or solenoid, is given by $B=kNI$, where k is a parameter that depends upon the geometry, N is the number of turns in the coil, and I is current through the coil, in amperes. This relationship is valid for DC as well as for time dependent currents up to frequencies that involve magnetic resonance of molecules. The magnetic field strength H, which produces magnetic flux in a material, is created when current passes through a coil. It is related to the magnetic flux density in a material by $B=\mu \cdot H$, where $\mu$ (mu) is the permeability, a parameter that defines the effect of H inside the material. In ferrous materials, such as carbon steel, the permeability can be 1000 or more. The permeability in air, or in the human body is 1, depending on the choice of units. Thus, a given electromagnetic field strength can be produced by a coil with a small number of turns and a large current or a coil with a large number of turns and a small current. In the electric circuit of FIG. 1, a 12 volt battery is described as the power source. In the embodiment of FIG. 1, the current through the coil 12 is determined largely by the voltage supplied by the power source 14 and the circuit resistance. The electrical resistance of the circuit is due to the resistance of the wire 26 and the contact resistance of contactors 42 and 44 with metal oxide accumulation on the surfaces. The resistance of the wire is a linear function of the wire cross-sectional area which may be expressed in a wire gauge number.

The treatment apparatus 10 may be adapted to different therapeutic applications by interchangeable induction coils 12 and power supplies 10. For example, a set of storage batteries 14 having different voltage and current ratings may be selectively substituted for the battery 14 as described above. Similarly, a set of induction coils 12 of different size and shape and having a different wire size and number of windings may be substituted for the induction coil 12. The following table lists a set of six different induction coils of different physical size and having coil windings of different number of turns. This table also shows the part of the body for which it is applicable.

| COIL NO. | LENGTH | DIAMETER | WIRE GAGE | WIRE LENGTH | USE |
| --- | --- | --- | --- | --- | --- |
| 1 | 8" | 3" | 10 | 35' | SMALL HANDS AND ELBOWS |
| 2 | 8" | 4" | 10 | 45' | LARGE HANDS AND ELBOWS |
| 3 | 8" | 6" | 10 | 60' | SHOULDERS AND KNEES |
| 4 | 8" | 10" | 10 | 60' | SHOULDERS AND KNEES |
| 5 | 8" | 42" | 10 | 80' | SHOULDERS |
| 6 | 8" | 60" | 10 | 100' | HIPS |

Induction coil #1 in the above table produces an electromagnetic field strength having a maximum value at the center of the coil of about 700 oersteds when the coil is energized by 12 volts across its terminals. Induction coil #6 in the above table produces a field strength having a maximum value at the inside periphery of the coil winding of about 2000 oersteds when the coil is energized with 12 volts across its terminals.

As described above, the striking contactors 42 and 44 are actuated manually to provide a switching of the treatment apparatus between on and off conditions. For turning the circuit on, the contactors are put in contact with each other and for turning the circuit off they are separated from each other. The contactors are switched on and off intermittently to generate current pulses. The sequential intermittent switching may be executed randomly in respect to on and off time intervals at the discretion of the operator. Also, the duration of the on time and the off time may be executed in accordance with a predetermined pattern. One preferred pattern for the treatment of arthritis, for example, comprises a sequence as follows: on-time one second duration followed by successive on-times of about one-tenth second spaced by time intervals of about one-tenth second. This pattern can be accomplished by a rubbing action of the movable contactor against the fixed contactor to produce the initial long pulse followed by a tapping action of the movable contactor against the fixed contactor in a continuous motion to produce about fifteen short interval pulses. Then this pattern is repeated for about three minutes with about fifteen seconds between patterns. This set of patterns may then be repeated several times in the discretion of the operator.

Figure 5:
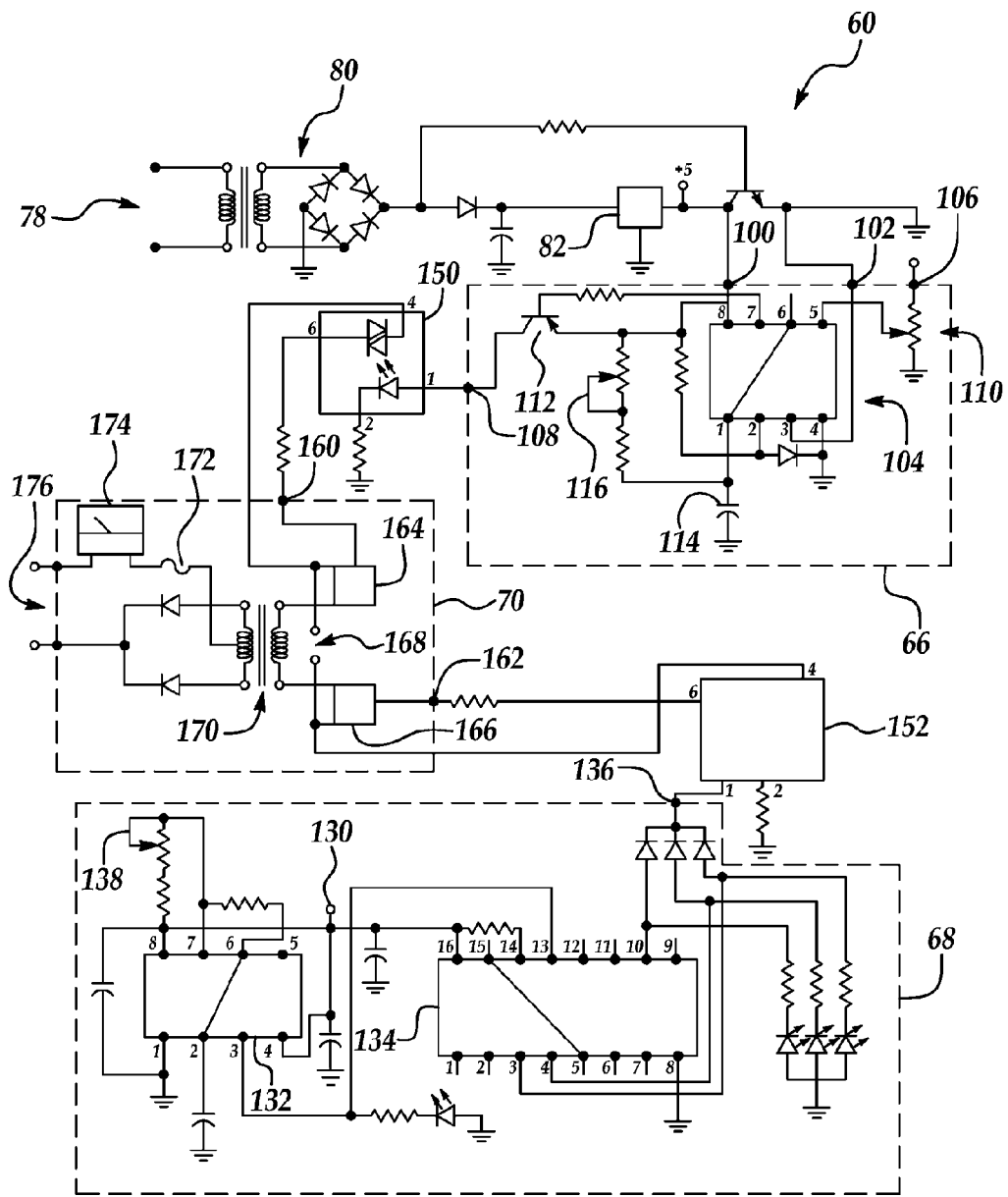
FIG. 5 shows a schematic of the electronic controller of FIG. 3.

According to another embodiment of this invention which is shown in FIG. 3, magnetic treatment device 58 includes induction coil 12 as before, but is energized by an electronic switching device 60 instead of the manually-operated switching device 16. Switching device 60 is an electronic controller that has the benefit of being powered by a widely available, conventional 110 VAC power source 62, and is capable of supplying induction coil 12 with a complex current waveform similar to that of the first embodiment without the necessity of the operator manually forming the current pulses. Furthermore, the current pulses are generated using solid state components to thereby simulate the effects of the arcing used in the first embodiment without the necessity of actually producing arc discharges. Turning now to FIG. 5, the circuitry of electronic power supply 60 is shown in detail.

Electronic controller 60 provides a consistent, yet adjustable stream of current pulses to induction coil 12 and generally includes a current circuit 66, a frequency circuit 68, and a driving circuit 70. A power input 78 receives power from a 110 VAC electrical outlet, and is connected to a transformer/rectifier unit 80 that steps down the input voltage to 12V and rectifies it to DC. To protect against variability in the magnitude of the 110 VAC input power, and hence variability in the stepped down and rectified signal, the transformer/rectifier unit 80 is coupled to a voltage regulator 82 which provides a steady 5 VDC signal to both the current circuit 66 and the frequency circuit 68.

Current circuit 66 controls the average current supplied to the induction coil 12 by adjusting the length or duration of each current pulse. Other means of adjusting the current can be used as well, such as by adjusting the repetition rate of the pulse or their peak magnitude, or by some combination of any of these. By controlling the length of each pulse, this circuit is able to control the average power associated with each current pulse, which in turn affects the electromagnetic field created by induction coil 12. According to the embodiment shown here, current circuit 66 generally includes power inputs 100 and 106, a pulse signal input 102, a pulse length adjustor 104, a signal output 108, and an adjustable operator input or potentiometer 110. As its name suggests, pulse length adjustor 104 is able to control the length or duration of each current pulse and can be implemented using an LM393 dual differential comparator, sold by National Semiconductor. According to this particular embodiment, 120 Hz pulses received by the first op-amp input on pin 3 of the LM393 are compared against a reference voltage of about 0.7 volts at pin 2 and cause the output of the op-amp at pin 1 to switch between zero and five volts at 120 Hz repetition rate. This causes charging and discharging of the capacitor 114 connected to pin 1. The resistor and trim potentiometer 116 assist in charging the capacitor from the +5 VDC source. Thus, this first op-amp is used as a waveform generator running at a 120 Hz rate. The output pin 1 of this waveform generator is connected to the negative differential input of the LM393's second op-amp and is compared against a reference voltage set between zero and five volts using potentiometer 110. When the voltage at pin 6 falls below this reference voltage due to discharging of the capacitor 114, the output pin 7 of this second op-amp goes to five volts, thereby preventing operation of the pnp transistor 112. When the waveform generator switches to allow charging of the capacitor 114, the input pin 6 at some point crosses over and exceeds the reference voltage at pin 5, causing the output pin 7 to go to zero volts, which in turn switches on transistor 112 and enabling current flow through the transistor. Thus, current circuit 66 provides a continuous series of pulses that are then used to cause driving circuit 70 to supply higher powered current pulses to the induction coil 12. By adjusting the reference voltage using potentiometer 110, the switching point of the output at pin 7 of the second op-amp can be controlled. In this manner, the pulse width can be adjusted within a wide range of duty cycles.

Frequency circuit 68 generates higher frequency components of the complex current pulses that are sent to the induction coil 12. These higher frequency components are superimposed on the current pulses generated using the current circuit 66. Frequency circuit 68 includes a power input 130, a timer 132, a counter 134, and a signal output 136. Power input 130 is connected to the +5 VDC power supply from linear regulator 82. According to the preferred embodiment shown here, timer 132 is an 8-pin integrated circuit such as the widely popular 555 timer originally introduced by Signetics Corporation (today, numerous versions of this timer are sold by a number of manufacturers). According to this arrangement, the 555 timer is configured as an astable multivibrator with a frequency that can be adjusted using a potentiometer 138. The output pin 3 of the astable is coupled to counter 134, which according to this embodiment is a 16-pin integrated circuit such as the widely available 4017 model. Counter 134 can be connected one of numerous ways, including the particular arrangement shown here where pins 3, 4 and 10 are signal outputs that are OR-tied together to form a single output signal, referred to as a frequency signal, that is sent to driving circuit 70 via output 136. The frequency signal sent by frequency circuit 68 dictates the frequency of the higher frequency components that are included in the current pulses delivered to induction coil 12, which in turn affects the corresponding electromagnetic field produced by the induction coil. By "higher frequency components" it is meant that the pulse signal sent by frequency circuit 68 is at a higher frequency than the repetition rate of the current circuit, and this higher frequency can be anywhere from several cycles per current pulse to frequencies that are orders of magnitude higher than the 120 Hz current circuit pulse rate.

For purposes of protecting the circuitry of circuits 66 and 68, optical couplers 150 and 152 are used to isolate pulse length circuit 66 and frequency circuit 68, respectively, from driving circuit 70. Each of the optical couplers allows for optical communication between the circuits so that the pulse length and frequency signals can be received by the power circuit without any direct electrical connection therebetween. A suitable optical coupler is the MOC 3022 optical isolator sold by a variety of manufacturers, including Motorola.

Driving circuit 70 utilizes the pulse signal from circuit 66 and the higher frequency signal from circuit 68 to provide induction coil 12 with a series of complex current pulses that are the same as or similar to that supplied by the apparatus of FIG. 1. The driving circuit generally includes signal inputs 160 and 162, triacs 164 and 166, a 110 VAC power input 168, a transformer 170, a fuse 172, an ammeter 174 and a pair of outputs 176. Signal input 160 carries the 120 Hz pulse signal and is coupled to the gate input of triac 164, which operates as a two-way SCR switch whose operational state is controlled by the pulse signal. Triac 164 is connected to both the 110 VAC power input 168 and transformer 170 so that when triggered, current can flow from the 110 VAC source through the triac to the transformer primary. Likewise, triac 166 is controlled by the frequency signal provided by frequency circuit 68, and is connected to both the 110 VAC power input 168 and the other end of the primary winding of transformer 170. For current to flow through the transformer primary, both triacs must be switched to a conductive state. In this manner the 120 Hz pulse signal from the current circuit and the higher frequency signal from the frequency circuit are combined together to create the complex current pulses. The transformer steps down the 110 VAC signal provided by the pair of triacs to a 24 VAC signal that is delivered to the induction coil 12 via a half-wave rectifier to thereby provide a continuous stream of 120 Hz pulses that include the higher frequency components generated by the frequency circuit 68. A fuse 172 is provided to help ensure that a maximum current, such as 30 amps, is not exceeded, and an ammeter 174 is provided to enable the operator to monitor the current supplied to the coil.

FIG. 4 includes an exemplary current pulse waveform outputted by the electronic controller 60 of FIG. 5. A pair of pulses A and B are shown which are generated by the current circuit 66, and each pulse includes higher frequency components throughout their duration. The higher frequency components are most evident at the trailing edge z of each pulse where the pulse tapers off more slowly.

The method of this second embodiment will now be described with reference to the magnetic treatment device 58 shown in FIG. 3, and in particular the electronic controller 60 shown in FIG. 5. The electromagnetic pulses produced by treatment apparatus 58 are caused by current pulses in the induction coil which varies as a function of time due to operation of electronic controller 60. The method is the same as discussed in conjunction with FIG. 1, except that rather than generating pulses using manually-operable contactors, the pulse are generated using the controller 60, with the operator controller the amount of current using the first potentiometer 110 and controlling the frequency of the higher frequency components using the potentiometer 138.

The inventor has treated over seventy different persons with the treatment apparatus and method of this invention. Some of these people were treated for complaints of arthritis, multiple sclerosis carpal tunnel, rotor cuff, tennis elbow and cancer. The inventor believes the treatments have been effective to reduce pain, produce curative effects and provide an improved quality of life.

It will thus be apparent that there has been provided in accordance with the present invention a magnetic treatment device, as well as a method of use which achieve the aims and advantages specified herein. It will of course be understood that the foregoing description is of preferred exemplary embodiments of the invention and that the invention is not limited to the specific embodiments shown. For instance, alternative circuit embodiments could be used in place of the electronic switching device, as it is not specifically limited to the precise embodiment shown herein. Various changes and modifications will become apparent to those skilled in the art and all such variations and modifications are intended to come within the scope of the appended claims.

As used in this specification and appended claims, the terms "for example," "for instance," and "such as," and the verbs "comprising," "having," "including," and their other verb forms, when used in conjunction with a listing of one or more components or other items, are each to be construed as open-ended, meaning that that the listing is not to be considered as excluding other, additional components or items. Other terms are to be construed using their broadest reasonable meaning unless they are used in a context that requires a different interpretation.

What is claimed is:

1. An electromagnetic treatment device for treating the body of a living creature via an electromagnetic field generated using electricity from a power source, comprising:
   an induction coil for creating an electromagnetic field in a selected part of the body; and
   a switching device having an input for receiving operating power from the power source and having an output connected to said induction coil to provide electrical power to said induction coil, said switching device providing said induction coil with current pulses to thereby produce a pulsed magnetic field extending through said induction coil, wherein said switching device includes circuitry that is switched between conductive and non-conductive states and that, during at least one transition between said states, generates said current pulses such that they include current fluctuations similar to those of an arc discharge, including higher frequency components of sufficient magnitude to cause said pulsed magnetic field to exhibit a complex waveform that includes multiple frequency components representative of said current fluctuations.

2. The electromagnetic treatment device of claim 1, wherein said switching device comprises a pair of striking contactors that can be manually manipulated to selectively switch said circuitry between said conductive and non-conductive states.

3. The electromagnetic treatment device of claim 1, wherein said switching device comprises an electronic controller that includes a current circuit that controls the amount of current supplied to said induction coil, a frequency circuit that creates the higher frequency components of said current pulses, and a driving circuit that includes said circuitry and that outputs said current pulses.

4. The electromagnetic treatment device of claim 3, wherein said electronic controller further includes a transformer/rectifier unit and a voltage regulator for supplying said current circuit and said frequency circuit with a regulated DC voltage.

5. The electromagnetic treatment device of claim 3, wherein said current circuit further includes a potentiometer for adjusting the average amount of current supplied to said induction coil.

6. The electromagnetic treatment device of claim 3, wherein said frequency circuit further includes a potentiometer for controlling the frequency of said higher frequency components of said current pulses.

7. The electromagnetic treatment device of claim 1, wherein each of said current pulses includes a leading edge, a trailing edge and a maximum current value, wherein said switching device is used to control the repetition rate of said current pulses and is used to provide the higher frequency components of said current pulses during at least the trailing edge of said current pulses.

8. The electromagnetic treatment device of claim 1, wherein said induction coil is a generally tubular component open at both axial ends, and includes a coil form supporting a coil winding.

9. The electromagnetic treatment device of claim 1, wherein a maximum strength of said electromagnetic field is in the range of about 500 oersteds to about 2,000 oersteds.

10. An electromagnetic treatment device for treating the body of a living creature via an electromagnetic field generated using electricity from a power source, comprising:
    an induction coil sized to fit over a selected part of the body, said induction coil including a winding having a number of turns of wire; and
    a switching device having an input for receiving operating power from the power source and having an output connected to said induction coil to provide electrical power to said induction coil, said switching device providing said induction coil with complex current pulses to thereby produce a pulsed magnetic field extending through said induction coil, at least some of said complex current pulses each including higher frequency components that occur during at least a portion of said current pulse;
    wherein said switching device produces said higher frequency components of said current pulses and can be manipulated to adjust the average amount of current delivered to said induction coil.

11. The electromagnetic treatment device of claim 10, wherein said switching device comprises a pair of striking contactors that can be manually manipulated to selectively open and close a circuit that supplies current to said induction coil.

12. The electromagnetic treatment device of claim 10, wherein said switching device comprises an electronic controller that includes a current circuit that controls the amount of current supplied to said induction coil, a frequency circuit that creates the higher frequency components of said current pulses, and a driving circuit that outputs said current pulses.

* * * * *